(12) United States Patent
Susko

(10) Patent No.: US 7,231,809 B2
(45) Date of Patent: Jun. 19, 2007

(54) OXYGEN MONITORING DEVICE

(76) Inventor: Kenneth Susko, 30 Amethyst St., Elmont, NY (US) 11003

( * ) Notice: Subject to any disclaimer, the term of this patent is extended or adjusted under 35 U.S.C. 154(b) by 0 days.

(21) Appl. No.: 11/198,132

(22) Filed: Aug. 8, 2005

(65) Prior Publication Data

US 2005/0270525 A1    Dec. 8, 2005

(51) Int. Cl.
*G01N 7/00* (2006.01)
(52) U.S. Cl. ..................... 73/31.05; 73/23.2
(58) Field of Classification Search ............ 73/31.05, 73/23.2
See application file for complete search history.

(56) References Cited

U.S. PATENT DOCUMENTS

| | | |
|---|---|---|
| 4,169,778 A | 10/1979 | Mann et al. |
| 4,178,222 A | 12/1979 | Murphy et al. |
| 4,538,575 A | 9/1985 | Chujo et al. |
| 4,636,293 A | 1/1987 | Bayha et al. |
| 4,708,777 A | 11/1987 | Kuraoka |
| 4,764,343 A | 8/1988 | Nyberg |
| 4,800,886 A | 1/1989 | Nestor |
| 5,153,931 A | 10/1992 | Buchanan et al. |
| 5,719,778 A | 2/1998 | Suzumura et al. |
| 6,071,476 A | 6/2000 | Young et al. |
| 6,925,852 B2 * | 8/2005 | Susko ............ 73/23.2 |

OTHER PUBLICATIONS

"Fatal Explosion Highlights Hazard of Flammable Vapors in Fuel Tanks", Air Safety & Security Trends, Policy and Regulation, *Air Safety Week*, Apr. 16, 2001, Washington, D.C. PBI Media LLC., vol. 15, No. 16, ISSN 1044-727X.

* cited by examiner

*Primary Examiner*—Hezron Williams
*Assistant Examiner*—Rodney Frank
(74) *Attorney, Agent, or Firm*—Buchanan Ingersoll & Rooney PC

(57) ABSTRACT

A gas monitoring device for monitoring gas levels within a chamber is provided. The gas monitoring device includes a housing having a probe with a sensor disposed on the probe. The probe extends through the housing and into a chamber such that the sensor is within the chamber. The housing includes a first passageway disposed about the probe and second passageway disposed about the first passageway. During operation of the gas monitoring device, a temperature adjusting medium enters the second passageway through an inlet of the housing and then enters into the first passageway via the second passageway. As the temperature adjusting medium travels through the first passageway, the temperature adjusting medium adjusts the temperature of the probe. The temperature adjusting medium adjusts the temperature of the probe through thermal conduction. As the temperature of the probe adjusts, the temperature of the sensor also adjusts through thermal conduction.

7 Claims, 3 Drawing Sheets

OXYGEN MONITORING DEVICE

BACKGROUND OF THE INVENTION

1. Field of the Invention

The present invention relates generally to gas sensing devices. More specifically, the present invention relates to a gas sensing device for measuring oxygen levels in fuel tanks.

2. Description of Related Art

Since 1959, a number of aircraft fuel tanks have unexpectedly exploded. Typically, the explosions occurred when an unknown ignition source ignited the fuel/vapor mixture in the fuel tank. Fuel/vapor mixtures are created during consumption of fuel within the fuel tank by engines of the aircraft. The consumed fuel leaves a space within the tank which generally fills with atmospheric air containing oxygen. The presence of both a flammable gas and the fuel/vapor mixture within the space creates the potential for an explosion within the fuel tank upon ignition. The industry has responded with various methods and apparatuses, as discussed in *Air Safety Week*, Vol. 15 No. 16, Apr. 16, 2001, *"Fatal Explosion Highlights Hazard of Flammable Vapors in Fuel Tanks."*

One prior art method which reduces fuel/vapor combustion includes the elimination of combustible gases from the fuel tank. This prior art method fills space within a fuel tank with an inert gas. The presence of the inert gas within the fuel tank deprives the fuel/vapor mixture of a flammable gas necessary for combustion. Nonetheless, the need to continuously fill the fuel tank with an inert gas and the attendant high costs associated therewith do not make this an attractive alternative for aircraft manufacturers.

A more efficient method in accordance with the prior art includes flooding the tank with inert gas when oxygen levels become high. This method requires continually measuring oxygen levels in a fuel tank. The sensors must stay at a constant temperature level in order to accurately measure oxygen levels. However, temperatures of fuel tanks in vehicles tend to fluctuate depending on the outside temperature. Therefore, the oxygen sensor's temperature must be kept at a constant level in order to allow accurate measurements by the oxygen sensor.

Prior art attempts to keep the temperature of a gas sensor constant include heating the gas sensor with electric resistance heaters when the temperature is low. However, these methods are not suitable for use in fuel tanks, as electrical current applied to the electrical resistance heaters may potentially ignite the fuel/vapor mixture within the tank, again making this an unattractive option for aircraft manufacturers.

Therefore, a need exists for a method and apparatus which maintains a temperature of a gas sensor at a constant level. This new method and apparatus should minimize the introduction of elements which may ignite a fuel/vapor or other hazardous mixture within a fuel tank and/or space.

BRIEF SUMMARY OF THE INVENTION

The present invention fills the aforementioned needs by providing a method and apparatus for maintaining a temperature of a gas sensing device which measures gas levels within a chamber which minimizes the introduction of elements which may ignite a medium within the chamber.

In one embodiment of the present invention, a gas sensing device having a housing, a probe and a passageway is disclosed. The housing includes a first end and a second end where the second end has an inlet and an outlet. The probe includes a fiber optic disposed within the housing and a sensor. The fiber optic extends through the housing such that an end of the fiber optic is adjacent the first end of the housing. The fiber optic end includes the sensor which senses gas surrounding the sensor. The passageway of the gas sensing device, which is disposed about the fiber optic, is in fluid communication with both the inlet and the outlet of the housing. The passageway conducts a temperature adjusting medium from the inlet to the passageway. The temperature adjusting medium adjusts a temperature of the probe and a temperature of the sensor through thermal conduction.

In another embodiment of the present invention, a method for maintaining a set temperature of a probe of a gas sensing device is disclosed. The probe of the gas sensing device extends through a passageway of a housing of the gas sensing device and into a chamber. The passageway of the gas sensing device includes an inlet and an outlet. The method comprises conducting a temperature adjusting medium through the passageway. The method also monitors a temperature of the probe during conduction of the temperature adjusting medium. The method adjusts an amount of the temperature adjusting medium conducted through the passageway in response to a monitored temperature of the probe where the monitored temperature differs from the set temperature of the probe. In this embodiment, adjusting the amount of the temperature adjusting medium conducted through the passageway adjusts the temperature of the probe through thermal conduction thereby maintaining the probe at the set temperature. Likewise, adjusting the amount of temperature adjusting medium conducted through the passageway also adjusts a temperature of a gas sensor disposed on an end of the probe through thermal conduction.

In a further embodiment of the present invention, an oxygen monitoring device is described. The oxygen monitoring device includes a housing, a first passageway, a probe and a second passageway. The housing includes a first end and a second end where the second end has an inlet and an outlet. The first passageway, which is disposed within the housing, is in fluid communication with the outlet of the housing second end. The probe is disposed within the first passageway and extends through the first passageway and beyond the housing at the housing first end. Furthermore, the probe includes a fiber optic having an end extending beyond the housing and a sensor. The sensor, which is disposed on the fiber optic end outside the housing, senses gas surrounding the sensor. The second passageway of the oxygen monitoring device is disposed about the first passageway. The second passageway is in fluid communication with both the inlet and the first passageway such that the second passageway conducts a temperature adjusting medium from the inlet to the first passageway for adjusting a temperature of the probe. When the temperature adjusting medium adjusts the temperature of the probe, the temperature of the sensor is also adjusts through thermal conduction with the probe.

As may be appreciated, the present invention provides a method and apparatus for maintaining a temperature of a gas sensor within a chamber while minimizing the introductions of elements which may combust flammable material located within the chamber.

BRIEF DESCRIPTION OF THE SEVERAL VIEWS OF THE DRAWING(S)

Many advantages of the present invention will be apparent to those skilled in the art with a reading of this specification in conjunction with the attached drawings, wherein like reference numerals are applied to like elements and wherein.

DETAILED DESCRIPTION OF THE INVENTION

The present invention provides a gas sensing device for sensing gas levels within a chamber. The gas sensing device includes a housing and a probe disposed within the housing having a tip extending from the housing into the chamber. The probe tip includes a gas sensor disposed thereon for sensing gas levels within the chamber. As will be discussed in greater detail with respect to the accompanying Figures, during operation, the gas sensing device maintains a temperature of the gas sensor via passageways disposed around the probe within the housing of the gas sensing device.

Figure 1:
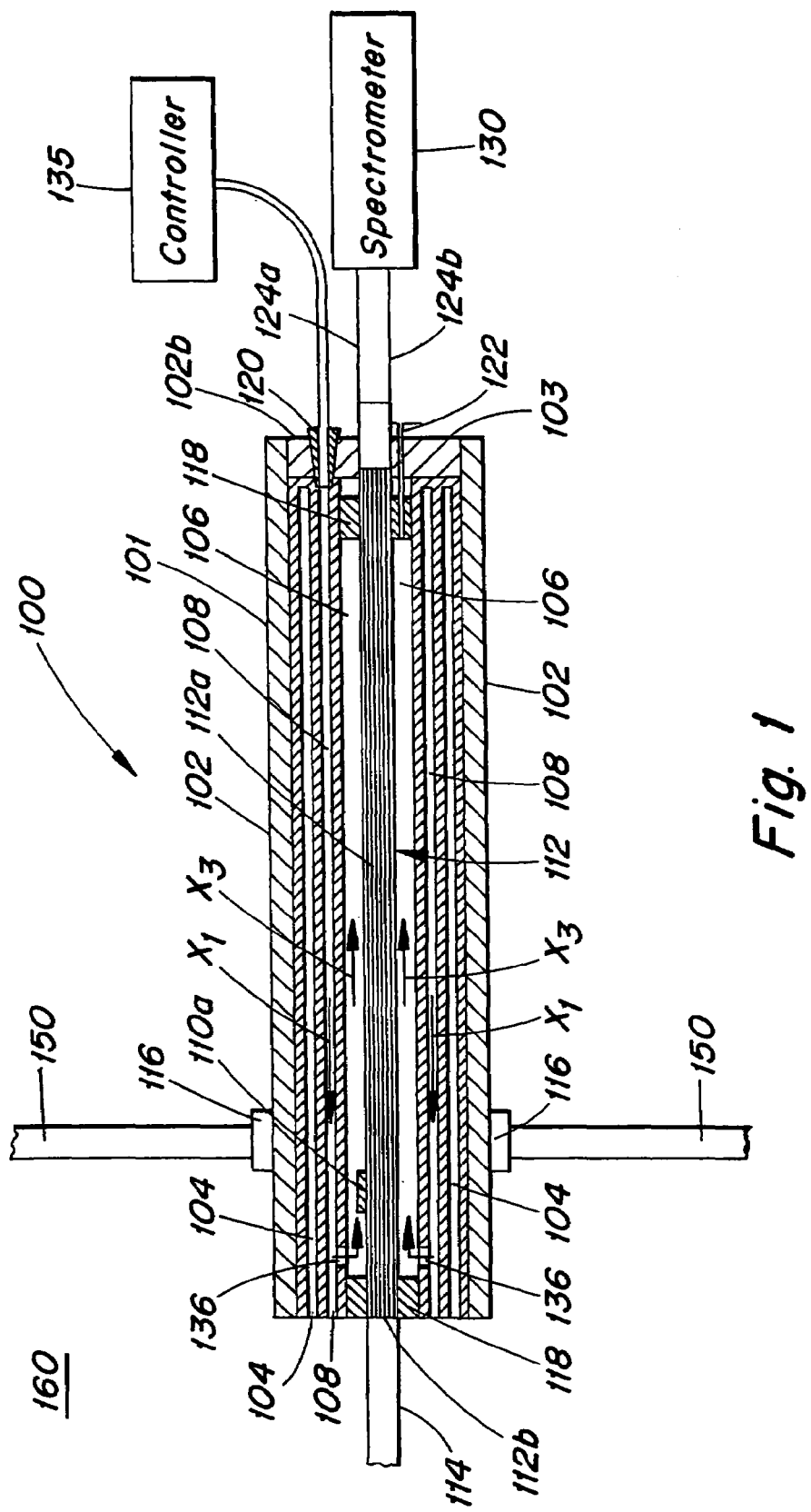
FIG. 1 illustrates a side view of a gas sensing device partially disposed within a chamber in accordance with an embodiment of the present invention.

Now making reference to the Figures, and more particularly FIG. 1, FIG. 1 illustrates a side view of a gas sensing device 100 partially disposed within a chamber 160 in accordance with an embodiment of the present invention. The gas sensing device 100 includes a housing 102, a probe 112 extending through the housing 102 and a sensor 114 disposed at an end 112b of the probe 112. The gas sensing device 100 also includes a first passageway 106 disposed about the probe 112 and a second passageway 108 disposed about the first passageway 106. A vacuum layer 104 surrounds the second passageway 108 thereby minimizing thermal losses of the gas sensing device 100. The gas sensing device 100 also includes an insulation layer 103 which encapsulates the gas sensing device 100. In this embodiment of the present invention, the insulation layer 103 may be vacuum chamber.

The housing 102 encloses the probe 112 and both the first and second passageways 106 and 108. The first and second passageways 106 and 108 communicate with one another via passages 136, as may be seen with reference to FIG. 1. The first passageway 106 fluidly communicates with an outlet 122 and the second passageway 108 fluidly communicates with an inlet 120. During operation of the gas sensing device 100, a temperature adjusting medium enters the gas sensing device 100 through an inlet 120 at an end 102b of the housing 102 and into the second passageway 108. After the temperature adjusting medium enters the second passageway 108, the temperature adjusting medium travels as indicated by directional arrows $X_1$. The temperature adjusting medium then enters into the first passageway 106 through the passages 136. Once the temperature adjusting medium enters the first passageway 106, the temperature adjusting medium contacts the probe 112 as it travels in a direction indicated by directional arrows $X_3$ towards the outlet 122, thereby adjusting a temperature of the probe 112 through thermal conduction. When the temperature of the probe 112 adjusts, the temperature of the sensor 114 also adjusts through thermal conduction. As may be seen with reference to FIG. 1, a controller 135 provides the temperature adjusting medium to the gas sensing device 100 in response to inputs received from the gas sensing device 100.

The controller 135 receives inputs from temperature sensors such as thermocouples 110a and 110b mounted within the gas sensing device 100. The thermocouple 110a mounts on the probe 112 within the first passageway 106, as shown with reference to FIG. 1. The thermocouple 110b mounts on the sensor 114 within the chamber 160. The thermocouples 110a and 110b may be any thermocouple suitable for monitoring temperatures of in-situ probes and gas sensors, such as platinum RTD, J-K thermocouple or other temperature sensors and thermocouples known in the art.

During operation of the gas sensing device 100, the thermocouples 110a and 110b provide data to the controller 135 which may be used to ascertain the temperature of the sensor 114 and the probe 112 as more fully discussed with reference to commonly owned application Ser. No. 09/994,714 filed on Nov. 28, 2001, the specification of which is herein incorporated by reference in its entirety. Using the data acquired from the thermocouples 110a and 110b, the controller 135 adjusts the amount of temperature adjusting medium traveling into the gas sensing device 100. To further illustrate, if data received by the controller 135 from the thermocouple 110a indicates that the temperature of the sensor 114 exceeds an optimal operating temperature of the sensor 114, the controller 135 reduces an amount of temperature adjusting medium entering the gas sensing device 100. According to an embodiment of the present invention, when the controller 135 reduces the amount of temperature adjusting medium entering the gas sensing device 100, the temperature of the sensor 114 and probe 112 decreases. Furthermore, in accordance with an embodiment of the present invention, the temperature adjusting medium may be any medium capable of adjusting a temperature of the probe 112 and the sensor 114, such as air, a liquid or the like.

It should be noted that in the above-described example, the controller 135 may also increase the amount of the temperature adjusting medium traveling into the gas sensing device 100 in order to increase the temperature of the sensor 114. Moreover, in accordance with an alternative embodiment of the present invention, a cooling temperature adjusting medium may be used where the controller 135 reduces the amount of temperature adjusting medium entering the gas sensing device 100 in order to increase the temperature of the sensor 114. Likewise in this embodiment, the controller may increase the amount of temperature adjusting medium entering the gas sensing device 100 in order to reduce the temperature of the probe 112 and the sensor 114.

It should also be noted that in a further embodiment of the present invention, the controller 135 may also adjust the temperature of the temperature adjusting medium in response to the temperature of the sensor 114. For example, if the controller determines that the temperature of the sensor 114 exceeds a predetermined value, the controller may decrease the temperature of the temperature adjusting medium while holding constant the flow rate of the temperature adjusting medium into the gas sensing device 100. Alternatively in this embodiment, if the controller 135 determines that the temperature of the sensor 114 is below a predetermined value such as a set temperature, the con troller 135 may increase the temperature of the temperature adjusting medium while keeping constant the flow rate of the temperature adjusting medium into the gas sensing device 100 constant thereby increasing the temperature of the sensor 114.

The gas sensing device 100 monitors the presence of gas within the chamber 160 via the sensor 114. The chamber 160 may be any structure capable of holding a medium, such as a fuel tank, a food storage bin or the like. In an embodiment where the chamber 160 is an aircraft fuel tank, the sensor 114 may be an optical device, such as an optical oxygen sensor, capable of monitoring oxygen levels within the chamber while not introducing electric current to the tank. In this embodiment, optical oxygen sensors function by sending light through an optical fiber to a thin coating such as hydrophobic sol-gel containing a ruthenium complex. The light from the optical fiber excites the ruthenium complex, thereby causing fluorescence. While in the sol-gel, if the excited ruthenium complex contacts an oxygen molecule, the flourescent signal is quenched thereby preventing collection of light energy by the fiber optic. Therefore, the amount of energy collected by the fiber optic is proportionate to the number of oxygen molecules present in the sol-gel. The optical fiber collects the fluorescence light energy and carries the light energy to a spectrometer. The spectrometer converts the light energy to digital data for oxygen level determination.

The amount of energy collected by the fiber optic is also proportionate to the temperature of the sol-gel. The temperature of the sol-gel effects the diffusion coefficient of oxygen in the sol-gel as well as the frequency of collision in the sol-gel between oxygen molecules and the excited ruthenium complex. Therefore, the temperature of the sol-gel must remain constant to ensure accurate readings of oxygen levels within the fuel tank. An example of a sensor which may used as the sensor 114 includes a Foxy Fiber Optic Oxygen Sensor available from Ocean Optics, Inc. located in Dunedin, Fla.

In an embodiment where the sensor 114 is an optical sensor, the probe 112 includes fiber optics 124a and 124b which couple with a spectrometer 130, as may be seen with reference to FIG. 1. During operation, the fiber optics 124a and 124b monitor the presence of oxygen within the chamber 160 via the sensor 114. The fiber optics 124a and 124b send information gathered by the sensor 114 to the spectrometer 130 for oxygen level determination within the chamber 160.

The gas sensing device 100 interfaces with the chamber 160 with a compression fitting 116. The compression fitting 116 may be any device suitable for interlocking the gas sensing device 100 with the chamber 160 such as compression fittings available from Swagelok™ located in Solon, Ohio. In addition to the compression fitting 116, the gas sensing device 100 also includes interfaces 118. The interfaces 118 hold the probe 112 as shown with respect to FIG. 1 such that as the temperature adjusting medium travels through the first passageway 106, the temperature adjusting medium surrounds the probe 112, thereby improving thermal conduction between the temperature adjusting medium and the probe 112.

Figure 2:
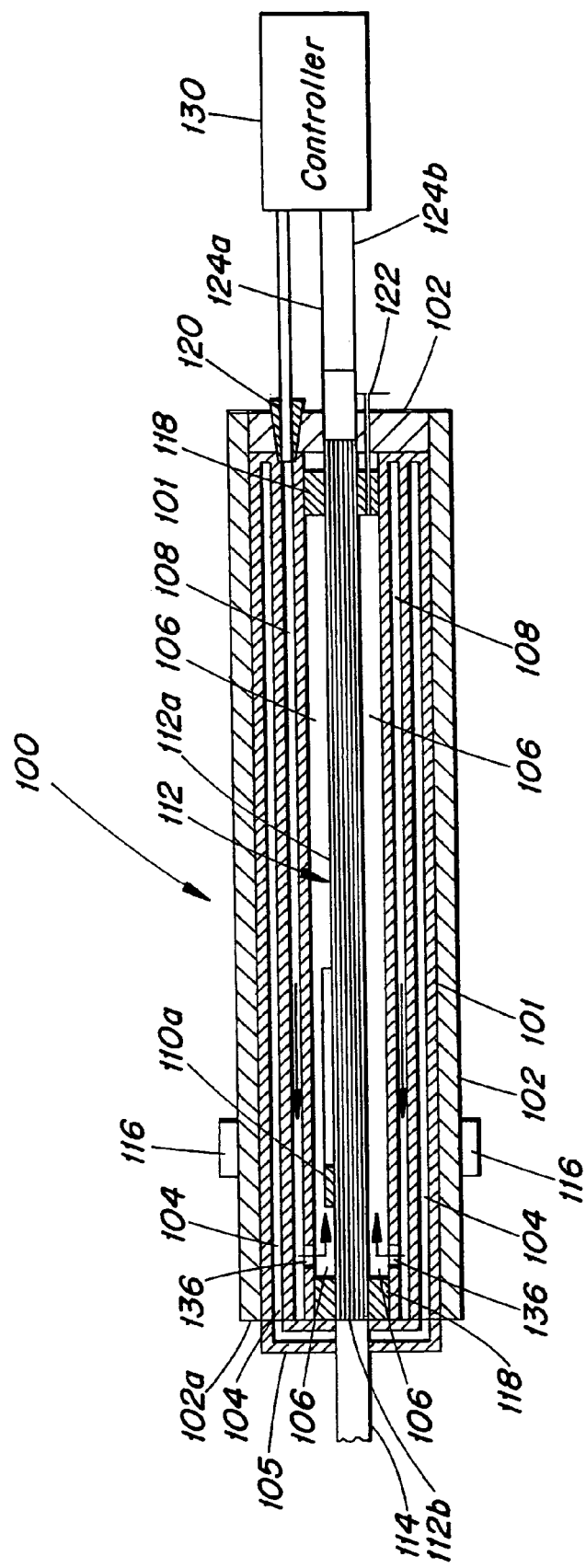
FIG. 2 is a side view of a gas sensing device having an enclosure in accordance with an embodiment of the present invention.

Now turning attention to FIG. 2, FIG. 2 illustrates an alternative embodiment of the gas sensing device 100 shown with reference to FIG. 1, where the gas sensing device 100 includes an enclosure 105. As may be seen with reference to FIG. 2, the enclosure 105 resides at a first end 102a of the housing 102 adjacent the sensor 114. The enclosure 105 extends both the insulation layer 103 and the vacuum layer 104 such that the vacuum layer 104 extends around the end of the gas sensing device 100 at first housing end 102a, thereby increasing thermal stability of the gas sensing device 100. In addition, the enclosure 105 may seal an end of both the first and second passageways 106 and 108. Alternatively, the enclosure 105 may also extend the second passageway 108. It should be noted that the gas sensing device 100 may be used for other applications including pharmaceutical, biomedical and food industry applications where chambers having mediums requiring sterile environments are used.

Figure 3:
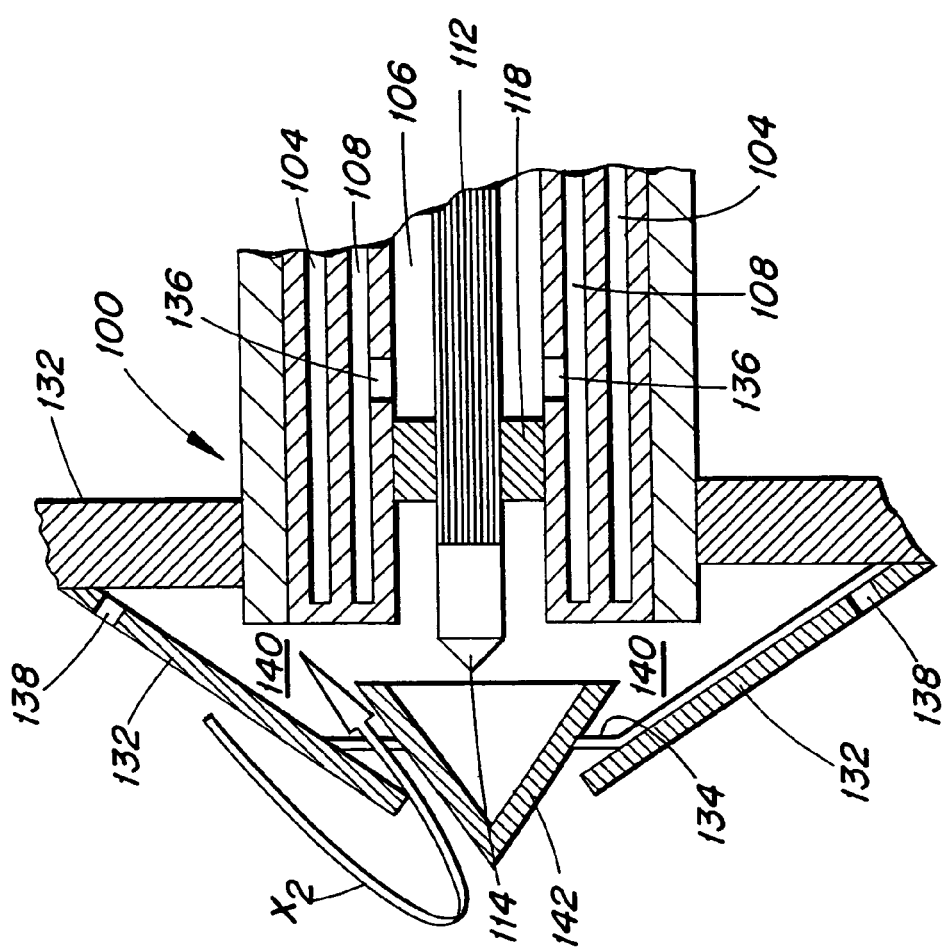
FIG. 3 illustrates the gas sensing device shown with reference to FIG. 1 with a shield disposed thereon in accordance with an embodiment of the present invention.

Now making reference to FIG. 3, FIG. 3 illustrates the gas sensing device 100 shown with reference to FIG. 1 with a shield 132 in accordance with an embodiment of the present invention. The shield 132 may be compression fit onto the gas sensing device 100 using any suitable technique. The shield 132 includes a shroud 142 disposed immediately adjacent the sensor 114, as may be seen with reference to the Figure. The shroud 142, which is held in place with struts 134, protects the sensor 114 from a medium disposed within the chamber 160 during operation of the gas sensing device 100. In this embodiment of the present invention, the struts 134 are constructed from a gas permeable material which permits passage of gases from the chamber 160 into a volume 140 of the shroud 142. Gases monitored by the sensor 114 travel through the shield 132 as indicated by directional arrow $X_2$ and into the volume 140 for monitoring. Therefore, the struts 134 allow monitoring by the sensor 114 of substances within the chamber 160. An example of a material which may be used for the construction of the struts 134 is Gore-Tex™ available from W.L. Gore & Associates, Inc. located in Newark Del. It should be noted that during operation of the gas sensing device 100, should medium enter the volume 140, the shield 132 includes passageways 138 which allow for passage of the medium from the volume 140 into the chamber 160.

The present invention provides an apparatus which may be used to monitor the presence of oxygen in a fuel tank having a fuel/vapor mixture. In addition, the present invention provides a method and device for maintaining a temperature of a gas sensor at a constant level within a fuel tank. The present invention maintains the temperature of a gas sensing device within a fuel tank with a temperature adjusting medium, such as air. As such, the present invention minimizes the introduction of elements, such as electric current, which may cause combustion of a fuel/vapor mixture within the fuel tank. Therefore, the present invention provides an attractive solution for monitoring gases within chambers.

Moreover, the present invention provides a sensor which may be used to monitor gases in a variety of applications. These applications include, but are not limited to, biomedical, pharmaceutical, food industry, heating, ventilating-air conditioning (HVAC) applications.

The above are exemplary modes of carrying out the invention and are not intended to be limiting. It will be apparent to those of ordinary skill in the art that modifications thereto can be made without departure from the spirit and scope of the invention as set forth in the accompanying claims.

What is claimed is:

1. A method for maintaining a set temperature of a probe of a gas sensing device, the probe extending through a passageway of a housing of the gas sensing device and into a chamber, the passageway including an inlet and an outlet, the method comprising:

conducting a temperature adjusting medium through the passageway;

monitoring a temperature of the probe;

adjusting an amount of the temperature adjusting medium conducted through the passageway in response to a monitored temperature of the probe where the monitored temperature differs from the set temperature of the probe, wherein adjusting the amount of the temperature adjusting medium conducted through the passageway adjusts the temperature of the probe through thermal conduction thereby maintaining the probe at the set temperature.

2. A method for maintaining a set temperature of a probe of a gas sensing device as recited in claim 1, wherein the temperature adjusting medium is air.

3. A method for maintaining a set temperature of a probe of a gas sensing device as recited in claim 1, wherein the probe further includes a sensor disposed at an end of the probe where the sensor is in thermal communication with the probe.

4. A method for maintaining a set temperature of a probe of a gas sensing device as recited in claim 3, wherein the probe further includes a fiber optic.

5. A method for maintaining a set temperature of a probe of a gas sensing device as recited in claim 4, wherein the sensor is a coating disposed on an end of the fiber optic.

6. A method for maintaining a set temperature of a probe of a gas sensing device as recited in claim 5, wherein the operation of monitoring a temperature of the probe further includes monitoring a temperature of the sensor.

7. A method for maintaining a set temperature of a probe of a gas sensing device as recited in claim 6, the method further comprising:

adjusting a temperature of the temperature adjusting medium in response to a monitored temperature of the probe where the monitored temperature differs from the set temperature of the probe, wherein adjusting the temperature of the temperature adjusting medium adjusts the temperature of the probe through thermal conduction and a temperature of the sensor through thermal conduction thereby maintaining both the probe and the sensor at the set temperature.

* * * * *